United States Patent [19]

Vida

[11] 3,947,443
[45] Mar. 30, 1976

[54] PROCESS FOR PREPARING 1,3-BIS(HALOMETHYL)PHENOBARBITALS

[75] Inventor: Julius A. Vida, Billerica, Mass.

[73] Assignee: The Kendall Company, Walpole, Mass.

[22] Filed: May 17, 1974

[21] Appl. No.: 471,042

[52] U.S. Cl. .............................................. 260/257
[51] Int. Cl.² ..................................... C07D 239/62
[58] Field of Search .................................. 260/257

[56] References Cited
UNITED STATES PATENTS

| | | | |
|---|---|---|---|
| 3,595,862 | 7/1971 | Vida | 260/257 |
| 3,635,980 | 1/1972 | Vida et al. | 260/257 |
| 3,679,683 | 7/1972 | Gorbaty | 260/257 |

*Primary Examiner*—R. Gallagher
*Assistant Examiner*—Anne Marie T. Tighe

[57] ABSTRACT 1,3-Bis(halomethyl)phenobarbitals are prepared by reacting phenobarbital with formaldehyde and a chlorine source or a bromine source at a temperature of −10° to 200°C in the presence of a Lewis acid catalyst, the formaldehyde and bromine or chlorine source being employed in at least approximately twice the molar amounts of phenobarbital. These compounds are useful anticonvulsant agents.

8 Claims, No Drawings

PROCESS FOR PREPARING 1,3-BIS(HALOMETHYL)PHENOBARBITALS

This invention relates to a process for preparing 1,3-bis(halomethyl)phenobarbitals and particularly to a process for preparing 1,3-bis(chloromethyl)phenobarbital and 1,3-bis(bromomethyl)phenobarbital.

The 1,3-bis(halomethyl)phenobarbitals prepared according to the process of this invention are useful as anticonvulsant agents for treating convulsions and seizures in warm-blooded animals.

These 1,3-bis(halomethyl)phenobarbitals have been previously prepared by first synthesizing 1,3-bis(methoxymethyl)phenobarbital, then reacting it with an acyl halide such as acetyl chloride, acetyl bromide, benzoyl chloride, etc. This procedure is fully described in U.S. Pat. No. 3,711,607. While providing the desired 1,3-bis(halomethyl)phenobarbital compounds, the aforementioned process is commercially unattractive in view of the fact that the bismethoxy compound must first be prepared from phenobarbital.

Now it has been found in accordance with this invention that 1,3-bis(halomethyl)phenobarbitals can be readily and economically provided by reacting phenobarbital with formaldehyde and a halogen source under selected reaction conditions.

The preparation of 1,3-bis(halomethyl)phenobarbitals according to the process of this invention is particularly surprising and unexpected since U.S. Pat. No. 3,767,798 teaches that 1,3-bis(methoxymethyl)phenobarbital may be made by reacting phenobarbital in methanol or dioxane with formaldehyde in the presence of catalytic amounts of hydrochloric acid. Now it has been found that by employing specified molar amounts of a halogen source, the bis-halomethyl phenobarbital compounds are obtained directly from phenobarbital, obviating the necessity of first preparing 1,3-bis(methoxymethyl)phenobarbital.

More in detail, the process of this invention comprises reacting phenobarbital with at least two molar proportions of formaldehyde and at least two molar proportions of a chlorine source or a bromine source at a temperature of −10° to 200°C in the presence of a Lewis acid catalyst.

The halogen sources include hydrochloric acid and hydrobromic acid in the gaseous form; acyl halides such as acetyl chloride, acetyl bromide, propionyl chloride, butyryl chloride, chloroacetyl chloride, benzoyl chloride, phthaloyl chloride; mixtures of any of the above compounds, etc. Preferred are the acids, acetyl bromide and acetyl chloride.

The formaldehyde can be employed in any of its conventional forms such as formaldehyde, paraformaldehyde, trioxymethylene, etc. Preferably, paraformaldehyde is used in this process.

As previously mentioned, the reaction proceeds in the presence of a Lewis acid catalyst. Any Lewis acid catalyst can be employed, but preferred catalysts include stannic chloride, aluminum chloride, zinc chloride, stannic bromide, etc. While the reaction proceeds at temperatures ranging from −10° to 200°C, preferably temperatures from 25° to 100°C are employed.

Where the halogen source is a liquid, no solvent is required. However, diluents such as acetic acid and acetonitrile can be employed in the process of this invention, even in those cases where liquid halogen sources are utilized.

The desired bishalomethyl phenobarbitals are obtained in high yield and excellent purity and are readily isolated by conventional techniques.

The following examples will serve to illustrate the practice of this invention.

EXAMPLE 1

Acetic acid (40 ml.) was placed in a 500 ml. three-necked flask equipped with an overhead stirrer, a dropping funnel, a reflux condenser, and an inlet for gas introduction. To the acetic acid, acetyl chloride (20 ml.; 0.28 mole) was added, followed by the addition, with stirring, of phenobarbital (23.2 g.; 0.1 mole). Then paraformaldehyde (12.0 g.; 0.40 mole) was added to the resulting suspension, with stirring. The reaction mixture was maintained at room temperature, and saturated with gaseous hydrochloric acid. Then 5.0 g. of fused zinc chloride was added to the reaction mixture. After the addition of the zinc chloride had been completed, the reaction mixture was heated, with stirring, to 60°–70°C; upon heating at this temperature for 2 to 4 hours, a homogeneous solution was obtained. The solution was kept, with stirring, at 60°–70°C for a period of 50 hours. Then the reaction solution was cooled to room temperature, resulting in the precipitation of a solid material, poured into ice (about 200 g.) and the solid material filtered, washed with water and dried. The resulting crude product was purified by dissolving it in a boiling solvent mixture of acetone and absolute ethanol (1:1 by volume, 250 ml.), adding activated carbon (1 g.) to the boiling solution, filtering the boiling solution through a compacted layer of diatomeceous silica, and evaporating the acetone while replacing it with absolute ethanol. The total volume of the resulting solution was about 150 ml. Upon cooling, crystals separated from the solution. The flask was allowed to stand overnight, the crystals removed by filtration, washed with ethanol and dried in a vacuum dessiccator at 50°C to provide 25 g. (76% yield) of 1,3-bis(chloromethyl)phenobarbital, m.p. 150°–151°C. The ethanolic mother liquor was evaporated to provide an additional quantity of 1,3-bis(chloromethyl)phenobarbital (5 g.), m.p. 151°–152°C, resulting in a total yield of 30 g. of 1,3-bis-(chloromethyl)phenobarbital (90.5% yield). Thin layer chromatography (in 100% benzene) resulted in an $R_f$ of 0.8 (with a very slight impurity at 0.4).

Analysis—Calc'd for $C_{14}H_{24}O_3N_2Cl_2$: C, 51.08; H, 4.29; Cl, 21.54; N, 8.51; Found: C, 51.26; H, 4.27; Cl, 21.44; N, 8.64

EXAMPLE 2

Following the general procedure and employing the equipment described in Example 1, phenobarbital (23.2 g.; 0.1 mole) was reacted with acetyl chloride (50ml.; 0.7 mole) and paraformaldehyde (20 g.; 0.67 mole) in the presence of 5 ml. of stannic chloride. The only deviation from the procedure of Example 1 was that the reaction solution was heated at 60°–70°C for 72 hours, and neither gaseous hydrochloric acid nor acetic acid was employed. After purification, 29.2 g. (88% yield) of 1,3-bis(chloromethyl)phenobarbital, m.p. 151°–152°C was obtained.

The mixed melting point of the products of Examples 1 and 2 was not depressed. The $R_f$ obtained from a thin layer chromatography of the product of Example 2 was identical to that obtained in Example 1, further corroborating that 1,3-bis(choromethyl)phenobarbital )chloromethyl) had been obtained.

EXAMPLE 3

Example 1 was repeated with the following exceptions: 10.0 g. (0.33 mole) of formaldehyde; 50 ml. of acetic acid and 5 g. of anhydrous zinc chloride were employed. The amount of 26.3 g. (80% yield) of 1,3-bis(chloromethyl)phenobarbital, m.p. 151°–152°C was obtained. Thin layer chromatography and a mixed melting point with the product of Example 1 confirmed the identification of the product as 1,3-bis(chloromethyl)phenobarbita.

EXAMPLE 4

Acetyl bromide (100 g.; 0.81 mole) was placed in a 500 ml. three-necked flask equipped with an overhead stirrer, a dropping funnel and a reflux condenser. To the acetyl bromide, phenobarbital (23.2 g.; 0.1 mole) was added, followed by the addition, with stirring, of paraformaldehyde (15.0 g.; 0.5 mole). Then anhydrous stannic bromide (10 g.) was added. The resulting solution was cooled to 0°C and maintained at that temperature while adding dropwise, over a period of 30 minutes, 20.0 g. of a 48% aqueous hydrogen bromide solution (corresponding to 9.6 g.; 0.11 mole of hydrogen bromide). Then the solution was heated to reflux and kept at reflux for 20 hours. The reaction solution was cooled to room temperature, resulting in the precipitation of a solid material, and then poured into ice (about 200 g.) and stirred for a period of 6 hours. The solid material was filtered, washed with water and dried to provide 1,3-bis(bromomethyl)phenobarbital (40 g., 95.5% yield), m.p. 160°–161°C.

The product was recrystallized from chloroform (300 ml.) to yield purified 1,3-bis(bromomethyl)phenobarbital, (38 g., 91% yield), m.p. 160°–161.5°C.

Analysis—Calc'd for $C_{14}H_{24}Br_2N_2O_3$: C, 40.22; H, 3.37; Br. 38.23; N, 6.70; Found: C, 40.09; H, 3.33; Br, 38.41; N, 6.80

Both the product initially obtained and the recrystallized material gave only one detectable spot on a thin layer chromatogram (in 100% benzene $R_f$ 32 0.85).

What is claimed is:

1. A process for preparing 1,3-bis(chloromethyl) phenobarbital or 1,3bis-(bromomethyl) phenobarbital comprising the step of reacting phenobarbital with formaldehyde and a chlorine source or a bromine source selected from the group consisting of hydrochloric acid, hydrobromic acid, and acyl chlorides and bromides selected from the group consisting of acetyl chloride, acetyl bromide, propionyl chloride, butyryl chloride, chloroacetyl chloride, benzoyl chloride, phthaloyl chloride and mixtures of any of the above compounds at a temperature of −10° to 200°C in the presence of a Lewis acid catalyst, the formaldehyde and bromine or chlorine source being employed in at least approximately twice the molar amounts of phenobarbital.

2. The process of claim 1 wherein a temperature of 25° to 100°C is employed.

3. The process of claim 2 wherein a chlorine source is employed.

4. The process of claim 3 wherein hydrochloric acid is employed as the chlorine source.

5. The process of claim 3 wherein acetyl chloride is employed as the chlorine source.

6. The process of claim 2 wherein a bromine source is employed.

7. The process of claim 6 wherein acetyl bromide is employed as the bromine source.

8. The process of claim 1 wherein the Lewis acid catalyst is selected from the group consisting of stannic chloride, stannic bromide, aluminum chloride and zinc chloride.

* * * * *

UNITED STATES PATENT AND TRADEMARK OFFICE
CERTIFICATE OF CORRECTION

PATENT NO. : 3,947,443
DATED : March 30, 1976
INVENTOR(S) : Julius A. Vida

It is certified that error appears in the above-identified patent and that said Letters Patent are hereby corrected as shown below:

Col. 1, line 32, "phenobarbital" (first occurrence) should be plural;

Col. 2, line 68, after "phenobarbital", delete ")chloromethyl)";

Col. 3, line 12, "phenobarbital" is misspelled;

Col. 4, line 6, after "$R_f$", delete "32" and insert instead -- = --;

Col. 4, line 9, change "1,3bis-" to "1,3-bis".

Signed and Sealed this eighth Day of June 1976

[SEAL]

Attest:

RUTH C. MASON
Attesting Officer

C. MARSHALL DANN
Commissioner of Patents and Trademarks